United States Patent [19]

Brenholdt

[11] 4,160,913

[45] Jul. 10, 1979

[54] WEB SCANNING APPARATUS

[75] Inventor: Irving R. Brenholdt, Stratford, Conn.

[73] Assignee: St. Regis Paper Company, New York, N.Y.

[21] Appl. No.: 822,064

[22] Filed: Aug. 5, 1977

[51] Int. Cl.² ............................................. G01N 21/32
[52] U.S. Cl. .................................... 250/563; 250/572; 356/431
[58] Field of Search ................ 250/562, 563, 214 AG, 250/572, 209; 356/201, 204, 205, 200

[56] References Cited

U.S. PATENT DOCUMENTS

| | | | |
|---|---|---|---|
| 3,646,353 | 2/1972 | Bhullar et al. | 356/200 |
| 3,676,008 | 7/1972 | West et al. | 250/563 |
| 3,774,041 | 11/1973 | Kaneko et al. | 356/200 |
| 3,779,649 | 12/1973 | Bertoya et al. | 250/563 |
| 3,781,531 | 12/1973 | Baker | 250/562 |
| 3,797,943 | 3/1974 | Nagao et al. | 250/562 |
| 3,970,857 | 7/1976 | Buckson | 250/572 |

*Primary Examiner*—David C. Nelms
*Attorney, Agent, or Firm*—Pearne, Gordon, Sessions, et al.

[57] ABSTRACT

A flying spot is used to scan a web completely across the web from a leading to a trailing edge plus an additional distance on each side with the apparatus being initiated automatically as the leading edge is reached and ceasing an output when the trailing edge is reached. The web might be a paper web, for example, being scanned to determine the two edges, and also to determine defects including holes and wrinkles in the web. The flying spot is rectangular with the length of the rectangle parallel to the moving direction of the web and this flying spot rectangle traverses from one side to the other of the web. A hole in the web gives less than average reflected illumination to a detector, whereas a wrinkle gives increased illumination to the detector. The circuit differentiates the raw signal so that a hole or dark signal, gives a positive and then a negative going pulse, whereas a wrinkle, or lighter signal, gives a negative going pulse followed by a positive pulse. The circuit discriminates between the leading web edge, which is a negative going pulse after differentiation, and the negative initial pulse of a wrinkle. The circuit also discriminates between the positive going pulse of the trailing web edge and the positive initial pulse of a hole in the web. The foregoing abstract is merely a resume of one general application, is not a complete discussion of all principles of operation or applications, and is not to be construed as a limitation on the scope of the claimed subject matter.

16 Claims, 8 Drawing Figures

WEB SCANNING APPARATUS

BACKGROUND OF THE INVENTION

Many production processes having moving webs require the quality of the web to be inspected. There is a need for 100 percent area inspection of large width webs such as paper webs for defects such as holes, cuts, wrinkles, dirt, etc., at web velocities up to 5,000 feet per minute.

The web scanning systems presently available commercially or known to the inventor fall in the categories of point or slit scanners or multihead fixed field detectors. The point scanners include laser and television camera scanners going transversely of the web. The slit scanners are ones which have a slit disposed transversely of the web without any scanning of a beam and depend upon the moving web to establish inspection of the area of the web. The multihead fixed field detectors are ones wherein the individual heads scan only a small area of the web and the cumulative areas from all of the multiple heads lie across the web to permit inspection as the web is moved.

The disadvantages of the prior art scanning devices is that point scanners cannot provide 100 percent inspection of a moving web unless the web is moving at a very slow speed relative to the transversely moving point. The slit scanners, such as image dissectors, can provide 100 percent inspection, but require prohibitively intense and uniform illumination of the total area being scanned. Operation in the visible light spectrum requires special direct current illumination sources to eliminate modulation interference produced by normal alternating current industrial lighting systems. Multihead fixed field detectors are complicated by the fact that they require hundreds of detector/amplifier combinations each of which requires separate sensitivity or balance adjustments. The electrical output for a given web defect is directly proportional to web velocity necessitating a wide-band signal amplification system.

Most of these prior systems require illumination in close proximity to the web, either above or below the web. In many systems the web must be threaded through the sensor. All commercial systems of the prior art are expensive due to the complexity of manufacture, the requirement for special intense through-the-web illumination, or complicated on-line adjustments.

The problem to be solved is to construct a web scanning apparatus which obviates the above-mentioned disadvantages.

SUMMARY OF THE INVENTION

The problem is solved by a web scanning apparatus for a web movable along a path, comprising, in combination, a radiation detector, scanning means to establish a flying spot scanning path to periodically scan transversely of the moving web from one side to the other side of the web, means to irradiate at least the flying spot scanned portion of the web, means to transmit to said detector the image of the flying spot scanned portion of the web, a differentiator connected to differentiate the output of said detector, and an output characterization circuit connected to the output of said differentiator to characterize between increasing and decreasing signals relative to a normal output from said detector during scan of the web.

An object of the invention is to provide a web scanning apparatus which is reliable and simple in operation.

Another object of the invention is to provide a web scanning apparatus which may be mounted all on one side of the web to avoid threading the web through the sensor.

Another object of the invention is to provide a web scanning apparatus which will scan variable width webs and automatically adjust to the web width.

Another object of the invention is to provide a web scanning apparatus which discriminates between light and dark reflections from the web.

Another object of the invention is to provide a web scanning apparatus wherein a given portion of the web width is sampled as to average change in reflection to control the average gain throughout the entire web width.

Another object of the invention is to provide a web scanning apparatus wherein the sensor head is self-contained and even though no external light source is required, the sensor is unaffected by bright industrial illumination systems.

Another object of the invention is to provide a web scanning apparatus which may be enclosed in a volume readily hand held and which may be installed in a position remote from the web.

Other objects and a fuller understanding of the invention may be had by referring to the following description and claims, taken in conjunction with the accompanying drawing.

DESCRIPTION OF THE PREFERRED EMBODIMENT

Figures 1, 2, 3:
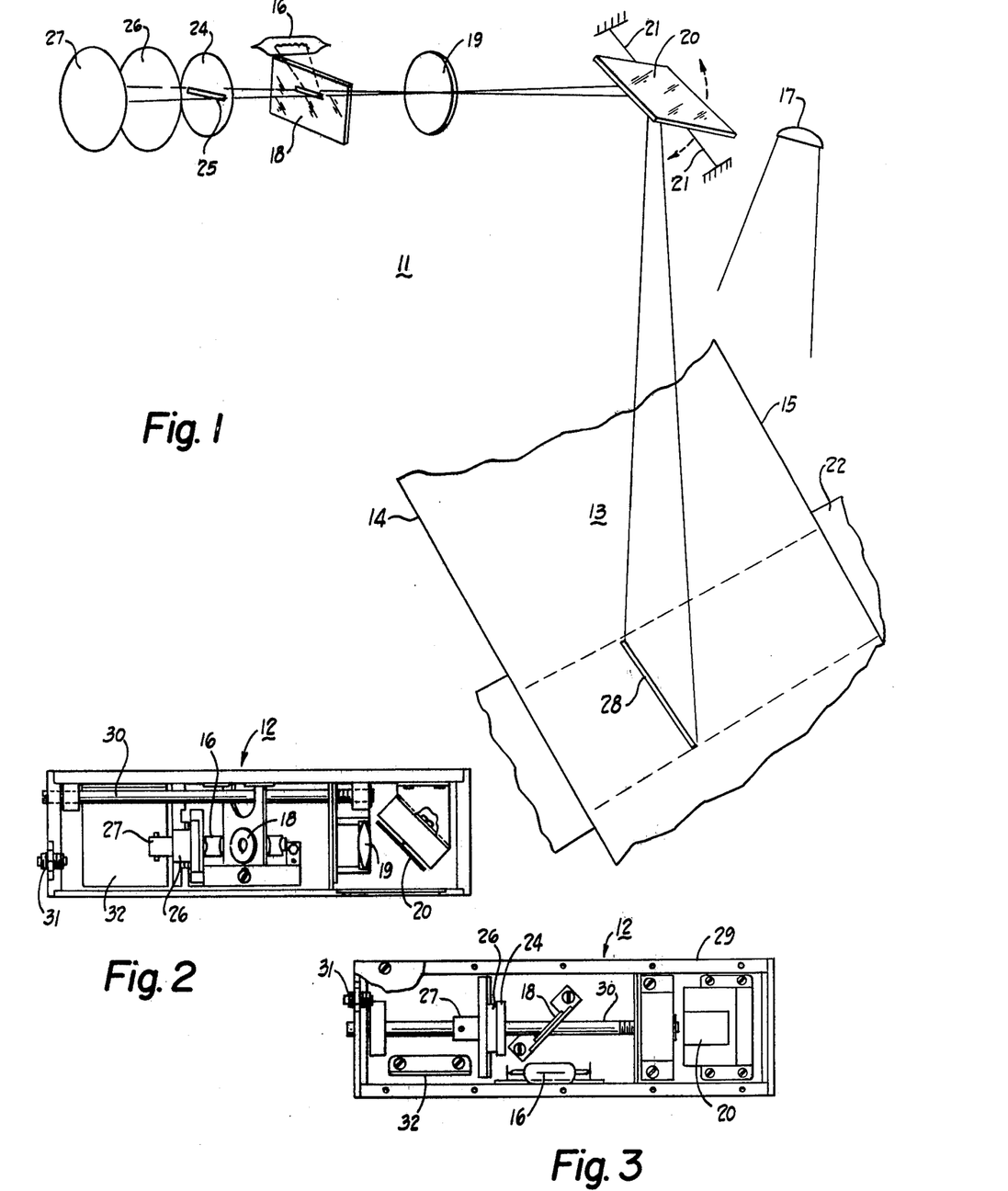
FIG. 1 is a perspective view of the mechanical components of the web scanning apparatus.
FIG. 2 is a side elevational view, with side plate removed, of the sensor and scanning unit.
FIG. 3 is a bottom view, with the bottom plate removed, of the unit of FIG. 1.

FIG. 1 is a perspective schematic diagram of the entire web scanning apparatus 11 and includes generally a scanning unit 12 so that a moving web 13 may be scanned from a first side 14 to a second side 15. A source of radiation is provided and in the preferred embodiment this is a source of illumination. This illumination source is preferably in the near infrared as established by a line source 16 or auxiliary flood lights 17 or both. The line source 16 may be an automotive 12 volt elongated filament lamp, for example, and the auxiliary flood lights may be ordinary lamps operating on commercially available voltage, for example 115 volt A.C. flood lamps, wherein two such lamps are connected in series to the 115 volt source so that each lamp operates at half voltage to be operating in the near infrared region and with extra long life for trouble free operation of the web scanning apparatus 11.

A beam splitter 18 reflects the light from the line source 16 through a lens 19 to a scanning mirror 20. The mirror 20 provides a means to scan transversely of the moving web 13. The scanning mirror may be a multifaceted rotating mirror or in the preferred embodiment is an oscillating mirror supported on taut bands 21 to help establish the period of oscillation.

A mask 24 provides an optical field stop and is provided with an enlongated slit 25 to pass radiation through a filter 26 to a photo-detector 27. The elongated slit 25 has a length at least ten times as long as its width and preferably about fifty times as long as its width. The image of this slit 25, as projected by the lens 19 onto the web 13, provides flying spot 28 which scans transversely of the web 13. Thus the elongated slit 25 limits geometrically the energy entering the photodetector 27 to that energy derived from the long narrow rectangle of the flying spot 28 at the plane of the web 13.

FIGS. 2 and 3 better show the details of construction of the scanning unit 12 which may include the line source 16 and with all parts mounted within a housing 29, except the auxiliary flood lights 17, so as to be a small volume which is readily hand held. A threaded rod 30 may be provided for focusing adjustment of the lens 19 and an electrical cable plug 31 may provide electrical connections to the parts within the scanning unit 12 including a printed circuit board 32 containing part of the electrical circuit described below.

The photodetector 27 may be a secondary emission photomultiplier, but preferably is a solid state broad band photodiode receptive to the near infrared spectrum. The optical filter 26 is one which passes near infrared radiation and excludes the ultra violet and most of the visible region of the optical spectrum. Efficient industrial illumination systems provide maximum radiation in the visible spectrum. In the United States this illumination is characterized by modulation at twice the power line frequency, usually 120 hertz. Industrial illumination systems which fall in this category include fluorescent mercury vapor and sodium vapor lamps. Industrial incandescent illumination systems produce maximum modulation, usually 120 hertz, in the visible spectrum and minimal modulation in the near infrared. All efficient industrial illumination systems produce either minimal radiation in the near infrared or minimal modulation of radiation in the near infrared.

Periodic variation of ambient illumination, the modulation as described above, may be deleterious to the functional performance of electro-optical systems in which the information format is radiant flux density versus geometry as a function of time. For these reasons the function of the optical filter 26 is to exclude radiation in the ultraviolet and visible region of the optical spectrum and to accept radiation in the near infrared.

The radiation source 16 or 17 is to provide illumination of the web or at least of that instantaneous area on the web which is the flying spot scanning path being viewed by the detector-slit combination. The line source may be an incandescent tungsten wire or ribbon used directly or in combination with a cylindrical lens or integrating cylinder. This source also may be a hot gas capillary. For maximum efficiency, the line source should be equal to the detector slit size in length and width, considering that the image of each is projected on the plane of the web 13.

The beam splitter 18 provides a means for superimposing the active image of the line source 16 on the passive image of the slit 25 at the plane of the web. The beam splitter may be an ordinary glass which reflects approximately two percent. It may be glass on which a molecular metallic deposit increases the reflection component of a light beam but allows some transmission through the element. Also the beam splitter may be a mirror having an aperture in its center or a mirror which occults some fraction of the beam. It is most convenient, but not a requirement, to orient the beam splitter at 45 degrees to the main optical axis.

The lens 19 forms an image of the slit 25 and the line source 16 at exactly the same place on the web 13. The lens diameter or aperture should be as large as is convenient to provide maximum transmission and reception of light to and from the web. The focal length of the lens is predicated by the parameters of distance to the slit 25, the equal distance to the line source 16, the distance to the web 13, and the desired image size at the web 13. The elongated image should have a component parallel to the longitudinal movement direction of the web 13 and in the preferred embodiment the length dimension of this flying spot rectangle 28 is parallel to the longitudinal movement direction of the web.

The function of the scanning mirror 20 is to move the superimposed images of the flying spot across the web in a scanning path periodically as the web moves under the sensor unit 12. The mirror 20 may be a rotating multi-faceted mirror but in the preferred embodiment is one mounted to oscillate on taut bands to thus eliminate problems with the bearings of the rotating mirror. Such oscillating mirrors may be oscillated several thousand times per second, and a larger mirror contemplated here, for example about one inch square, may be oscillated up to 100 times per second over a thirty degree range.

The printed circuit board 32 may include a preamplifier to amplify the output signal of the photo-detector 27.

Figure 4:
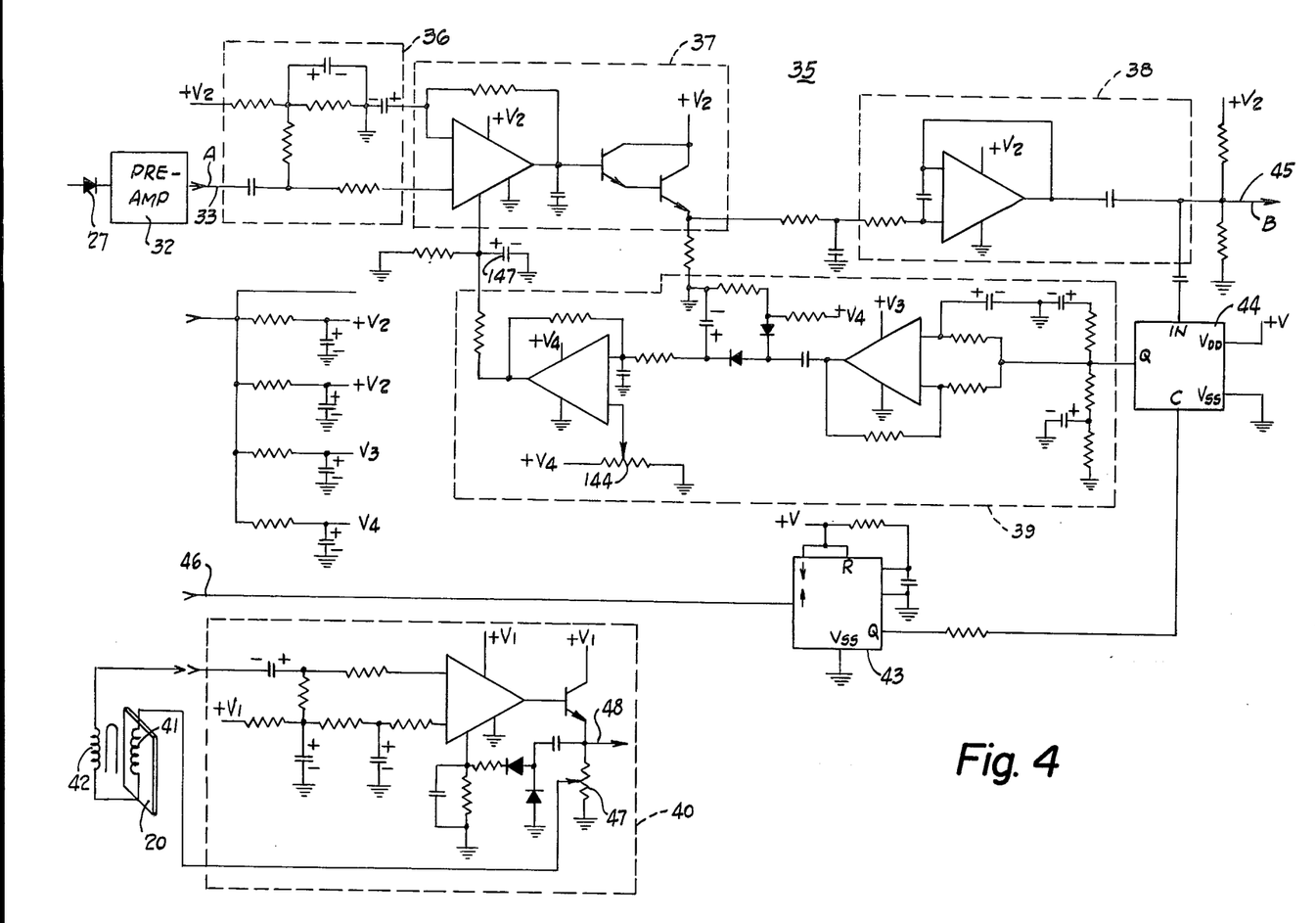
FIG. 4 is a schematic diagram of the differentiator and associated circuits connected with the photodetector.

FIG. 4 illustrates a second circuit board 35 which may be mounted at a remote location and connected by a cable to the cable plug 31. This circuit 35 includes a differentiator 36, a controlled gain amplifier 37, an active low pass filter 38, an AGC circuit 39, an oscillator 40 connected to a driver coil 41 to oscillate the mirror 20, a feedback coil 42 connected to the input of the oscillator 40, a one-shot multivibrator 43 and an analog switch 44. The filter 38 acts to discriminate against electrical noise by passing only the low frequency signal.

The output 33 of the preamplifier 32 is connected to the input of a differentiator 36 which supplies the amplifier 37. The gain of this amplifier is controlled by the AGC circuit 39 and the output signal, which will have some average value as the web is being scanned, is passed through the active low pass filter 38 to an output terminal 45. The oscillator 40 supplies from potentiometer 47 the drive signal to oscillate the mirror 20, and also has an output at a terminal 48. The one-shot multivibrator 43 has an input at terminal 46 to be turned on for a short time the analog switch 44 so that only a predetermined first portion of the width of the web is scanned and sampled as to average radiation reflected therefrom. This controls the AGC circuit 39.

Figure 5:
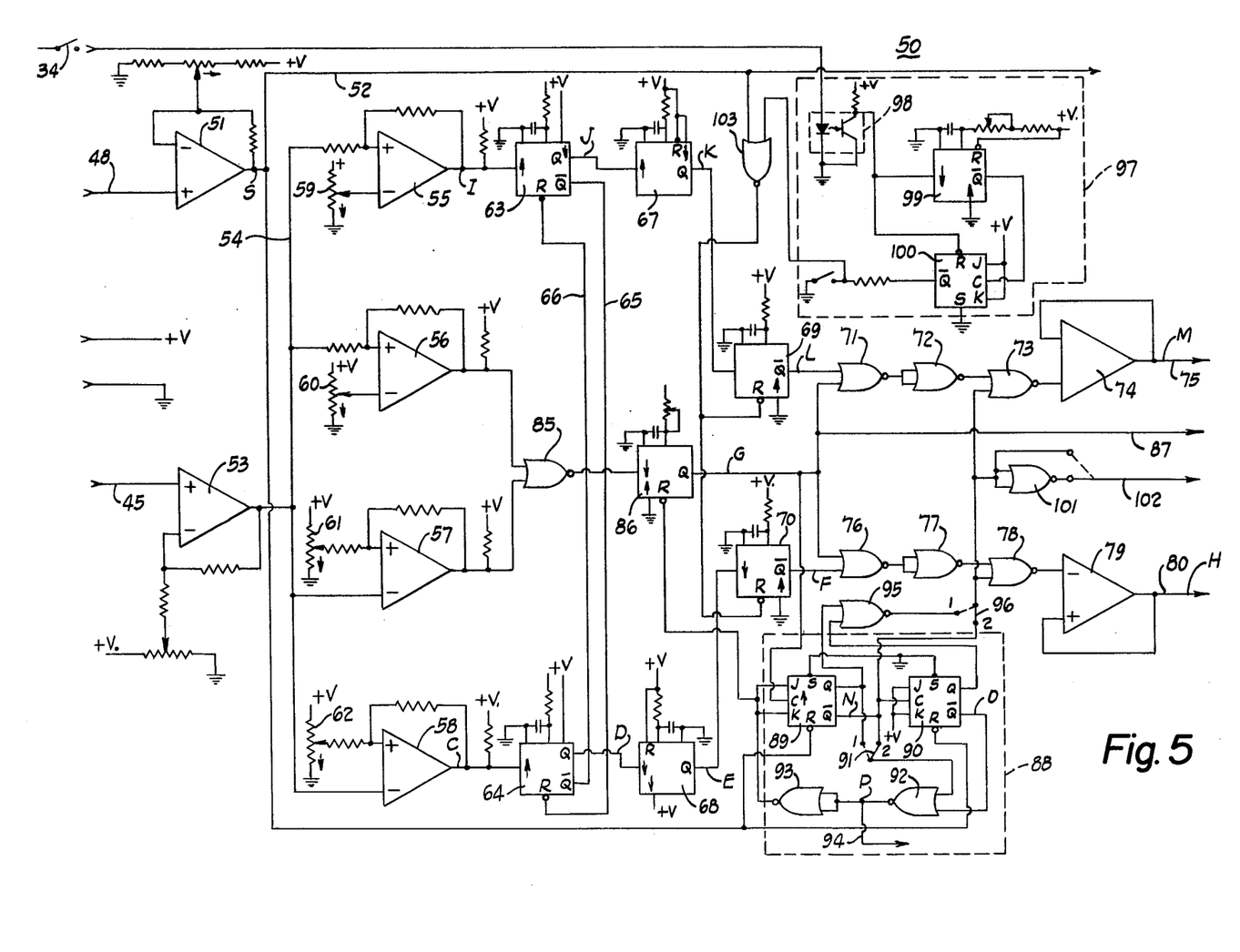
FIG. 5 is a schematic diagram of the output characterization circuit connected to the output of FIG. 2.

FIG. 5 shows a third circuit board 50. This circuit 50 includes the connection to a terminal 48 which supplies a squarer amplifier 51 to square the oscillator frequency by amplification. This signal is supplied on a conductor 52. The output signal from terminal 45 of the circuit 35 of FIG. 4 is supplied at the terminal 45 of FIG. 5. It is supplied as an input to an amplifier 53 and the output thereof is supplied to a conductor 54. This conductor supplies the inputs to four voltage regulators 55, 56, 57 and 58. the input from conductor 54 to these voltage comparators is to the non-inverting input on comparators 55 and 56 and to the inverting input on comparators 57 and 58. A positive threshold voltage is supplied by potentiometers 59 and 60 to the inverting inputs of comparators 55 and 56 and is supplied by potentiometers 61 and 62 to the non-inverting inputs of comparators 57 and 58.

The voltage comparators 55 and 58 supply their outputs to one-shot multivibrators 63 and 64, respectively. The $\bar{Q}$ outputs of these one-shots are connected to conductors 65 and 66, respectively, which are connected to the reset terminals of the other of these one-shots in a lock-out connection. The Q outputs of the one-shots 63 and 64 are connected to delay one-shots 67, 68, respectively. The Q outputs of the one-shots 67 and 68 are connected to one-shots 69 and 70, respectively.

The output of one-shot 69 is connected through NOR gates 71, 72 and 73 to an amplifier 74 and the output of this amplifier is a terminal 75. In a similar manner the one-shot 70 is connected through NOR gates 76, 77 and 78 to an amplifier 79 which has an output terminal 80.

The voltage comparators 56 and 57 have an output which is normally low and is connected to inputs of a NOR gate 85. The output is normally high and is connected to the trigger input of a one-shot 86, the Q output of which is connected to inputs of both NOR gates 71 and 76 and also connected to an edge signal output 87. An edge counter circuit 88 includes J, K flip flops 89 and 90 with the clock input to the flip flop 90 coming from the $\bar{Q}$ output of one-shot 86. With jumper 91 in the "2" position, the $\bar{Q}$ output of the flip flop 89 is connected through NOR gates 92 and 93 to the J, K input of flip flop 89, also to the reset terminal of one-shot 86. A large defect output terminal 94 is connected between the two NOR gates 92 and 93. The $\bar{Q}$ output of the flip flop 89 is also connected through the "2" position of a jumper 96 to an input of the NOR gates 73 and 78.

If the web is so wide that only one web edge is being scanned, then jumpers 91 and 96 are placed on the "1" position. In normal use, the scanning paths scans two web edges, so the jumpers are in the "2" position. If the jumpers are in the "1" position, then a NOR gate 95 is used. The outputs of flip flops 89 and 90 are connected as inputs to this gate 95, and the output thereof goes through jumper 96 to inputs of the NOR gates 73 and 78.

A time delay circuit 97 is connected with an input from a switch 34, which is closed when the web starts moving, through an optical coupler 98 to a one-shot multivibrator 99 and from the $\bar{Q}$ output thereof to a J, K flip flop wired as a set-reset flip flop 100. The $\bar{Q}$ output of this flip flop 100 is connected to an input of a NOR gate 103. This is a time delay to delay output of the circuit of FIG. 5 until the web has been started and reaches proper tension. The output of the NOR gate 95 through the jumper 96 also supplies a NOR gate 101 to a web pulse output terminal 102.

Figure 6:
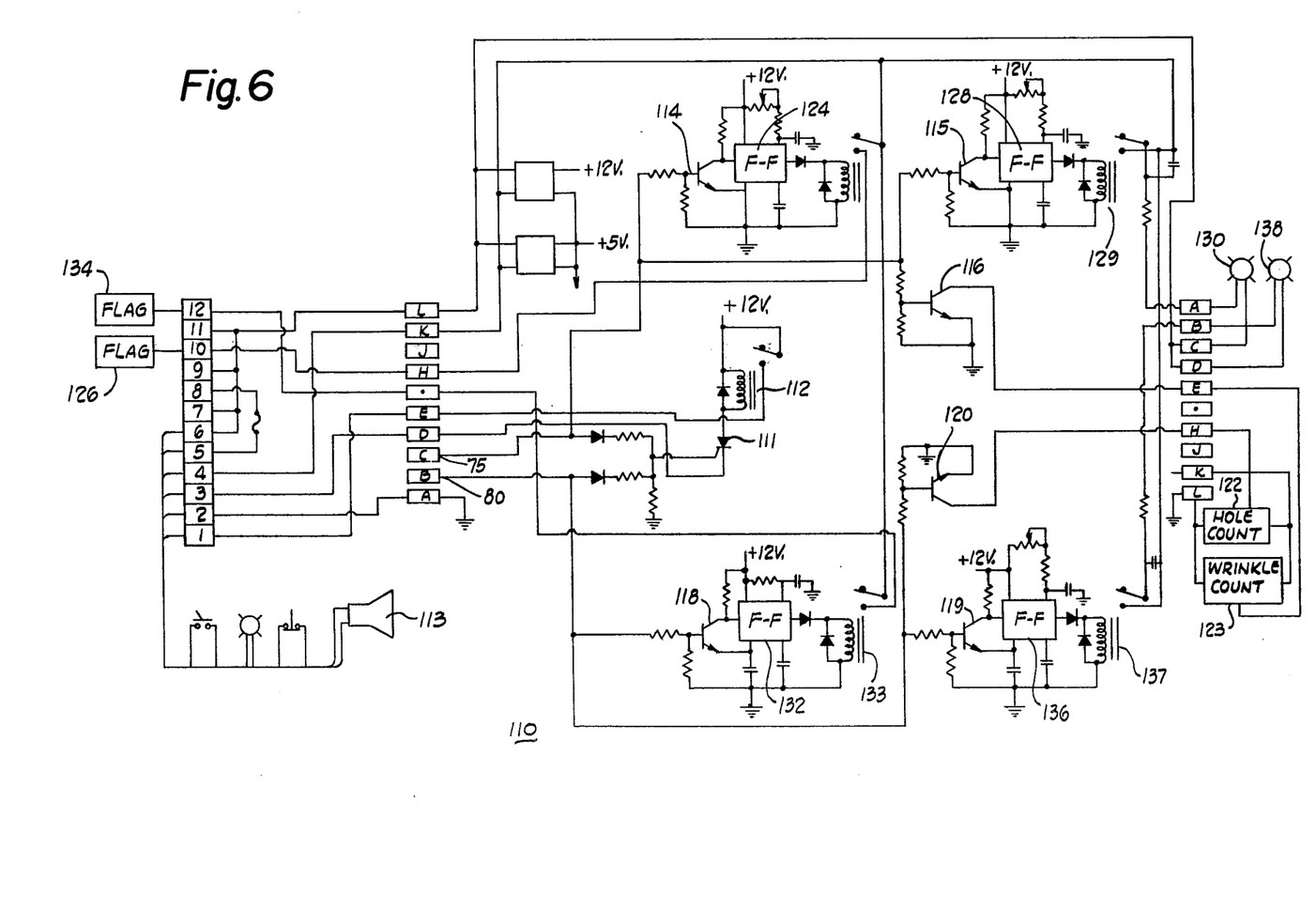
FIG. 6 is a schematic diagram of the output and alarm circuit.

FIG. 6 shows an alarm and count circuit 110 which has terminals 75 and 80 as inputs from the circuit 50 of FIG. 5. Both these terminals are connected in a wired OR connection to the gate of a thyristor 111 which energizes a relay 112. The closing of the contacts of this relay 112 will energize an alarm 113.

The output terminal 75 supplies a signal of one type of defect, for example, holes in the web 13. This output terminal is connected to energize three transistors 114, 115 and 116. The output terminal 80 of the circuit of FIG. 5 supplies a signal of another type of defect, for example wrinkles on the web 13. This terminal 80, in FIG. 6, is connected to energize transistors 118–120. The audio alarm 113 circuitry is common to both channels. The rest of the circuitry of each channel is identical but separate. The defect count pulse for a hole defect turns on the three transistors 114, 115 and 116 and for a wrinkle type defect turns on the transistors 118, 119 and 120. The energization of transistor 116 or 120 turns on a hole counter 122 or wrinkle counter 123, respectively, to count these defects. Energization of the transistor 114 turns on a monostable multivibrator 124 to act as a pulse stretcher. This energizes a relay 125, energizing a flag device 126 or a paint sprayer to spray the edge of the web at that point to identify the type and position of defect on the rolled up web product. Energization of transistor 115 energizes a monostable multivibrator 128 as a pulse stretcher to energize a relay 129 and thus energize an indicator lamp 130.

In a similar manner energization of the transistor 118, when a wrinkle is detected in the web, will energize a monostable multivibrator 132 as a pulse stretcher which energizes a relay 133 and the closing of the relay contacts will energize a flagging device 134 to flag the defect or may energize a paint sprayer to spray a different color on the web edge to identify the type and position of the wrinkle defect on the rolled up web product. The energization of transistor 119 energizes a monostable multivibrator 136 as a pulse stretcher which energizes a relay 137 and the closing of the contacts energizes an indicator lamp 138. The lamps 130 and 138 may be different colors to readily identify the different types of defects.

OPERATION

The oscillator 40 shown in FIG. 4 generates a sinusoidal voltage, at about 100 hertz as an example, in order to supply a driving voltage to the driver coil 41 to oscillate the mirror 20. With the system energized, the line source 16 is caused to sweep transversely a rectangular flying spot 28 transversely of the web 13. If the auxiliary flood lights 17 are used then the scanning area of the web 13 is entirely illuminated and it is the image of the slit 25 which is scanned in a scanning path transversely of the web 13. In either event the web is scanned transversely as it is moved longitudinally and the reflected radiation is provided to the detector 27. As an example, the image of the slit 25 on the web 13, as the flying spot 28, might be six inches long by ⅛ of an inch wide. At 100 hertz scanning rate, this will permit 100 percent inspection of the web for web speeds up to 50 feet per second or three thousand feet per minute. Higher scanning frequencies will permit higher web speeds. The web scanning apparatus 11 has been used to scan paper webs, as one example, and used to determine the edges of that web 13 as well as to detect two different types of defects in the web. With a dark background 22 at the scanning path, if a hole appears in the web 13, then the amount of light reflected to the detector 27 decreases. If a wrinkle is present in the web then the amount of light on the detector increases. Accordingly, the system permits detection of and discrimination between these two different types of defects. Also the system is quite sensitive and it has been determined that a small hole, for example only ⅛ inch in diameter, will change the output of the detector sufficiently to signal the presence of a hole. This was with the image of the slit on the flying spot 28 being six inches by ⅛ of an inch so that this is only about a two percent change in the average value of light reflected to the detector 27.

Figure 7:
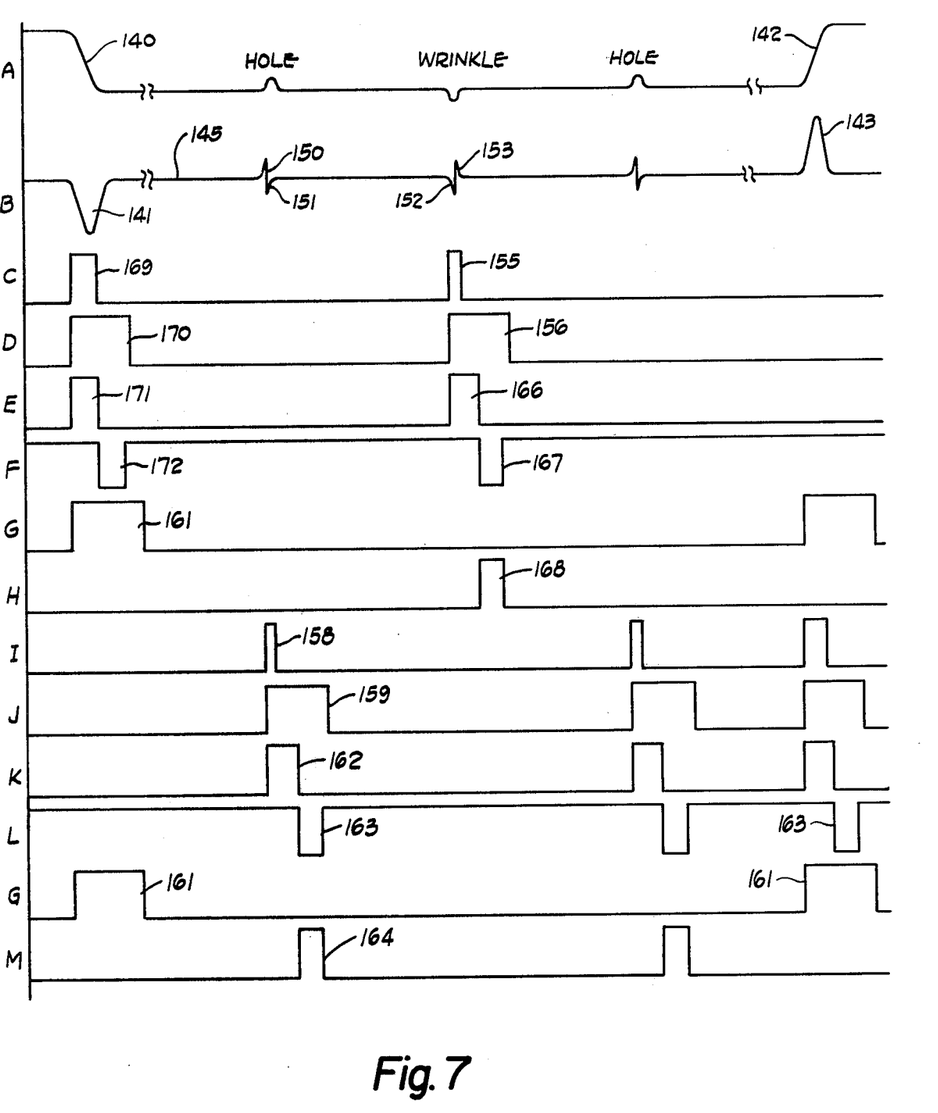
FIG. 7 is a graph of voltage pulses explaining the operation of the circuit.

As the flying spot 28 is sweeping across the web 13 there will be an average value of illumination so that the photodetector 27 has an average or nominal output, and FIG. 7 shows a curve A of the raw signal at point A, namely, the output of the photodetector 27, or it may be considered the output of the preamplifier 32. The mirror is driven with a sufficient excursion so that it sweeps beyond the edges 14 and 15 of the web 13. Accordingly, as the leading edge 14 is scanned curve A shows that a negative going output signal at 140 is developed. The differentiator 36 determines the rate of change of this negative going signal 140 and develops a negative going pulse 141 shown at curve B which is at the output terminal 45 of circuit 35 of FIG. 4. As the trailing edge 15 of the web is scanned a positive going signal 142 is developed by the detector 27 which gives a positive going pulse 143 on curve B at terminal 45. The AGC control circuit 39 may be adjusted at a potentiometer 144 so that the peak value of the pulses 141 or 143 will be within the desired range. Merely as an example, the average value during scan of the normal web 13 might produce a voltage of 7.5 volts DC on the output terminal 45, which on curve B would be the base line 145. The peak value of the pulses 141 and 143 might be 1.5 volts as an example.

An advantage of the present apparatus is that webs of variable width may be scanned and one need not have a circuit which is usable only with a fixed web width. Where webs of paper are to be scanned, the web width might vary from 18 inches to 60 inches or more and adjustment of a potentiometer 146 in the oscillator will adjust the scan driver voltage to change the excursion of the mirror 20 to suit the maximum web width. If 18 inches is an example of the narrowest web to be scanned in a particular paper making or paper using plant, then the length of time of the one-shot multivibrator 43 might be selected to coincide with 12 inches of scan of the web from the leading edge. The leading edge signal is applied at terminal 46 to turn on the one-shot 43. This therefore enables the analog switch 44 for only the first 12 inches of scan of the web. This means that the average change in reflection from the web for this first 12 inches is passed to the AGC circuit 39 which charges a capacitor 147 and this maintains a given level of automatic gain control on the amplifier 37 until the web is next scanned. The AGC circuit 39 is one wherein the first amplifier in the circuit amplifies the signal and the two diodes convert the signal into a DC level proportional to the signal amplitude. This DC level is subtracted from a DC level set by the potentiometer 144. The output of the second amplifier in the circuit provides the control current for the amplifier 37.

The circuit 50 of FIG. 5 is the output characterization circuit which evaluates the input signal shown at curve B on FIG. 7 and decides if any defects are present. If the circuit decides that a defect is present, then the type of defect, either a hole or wrinkle, is determined and an appropriate output pulse is generated on the output terminal 75 for a hole defect or on terminal 80 for a wrinkle defect. Wave form B in FIG. 7 shows a signal caused by a hole with a positive pulse 150 followed by a negative pulse 151. A signal caused by a wrinkle type of defect creates first a negative pulse 152 followed by a positive pulse 153. The signal caused by a hole defect or a dark contrast is called a hole signal and a signal caused by a wrinkle defect or light contrast is called a wrinkle signal.

This wave form B on the terminal 45 at the input of the circuit of FIG. 5 is amplified in the amplifier 53 and applied to the voltage comparators 55–58. The threshold level or bias level of the voltage comparators is set by the potentiometers 59–62 associated with each voltage comparator.

Assuming that the normal output during average scan of the web 13 establishes 7.5 volts DC on the conductor 54, then the potentiometers 59 and 60 are set at threshold levels greater than this value and the potentiometers 61 and 62 are set at threshold levels less than this value. As an example, potentiometer 59 might be set at 8 volts, potentiometer 60 at 8.5 volts, potentiometer 61 at 6.5 volts and potentiometer 62 at 7 volts.

Considering first a wrinkle signal, the negative going pulse 152 of the wrinkle signal will cause the comparators 58 and 55 to have output pulses in that order in time. The comparator 58 first has an output pulse 155, shown in curve C of FIG. 7, and this is supplied to the one-shot 64. The various one-shots on the circuits of FIGS. 4 and 5 have a small arrow thereon indicating whether they trigger on a positive or negative going input pulse. The one-shot 64 triggers on a positive going pulse so that the Q output goes high and the $\bar{Q}$ output goes low. This places a low signal on the conductor 66 to lock out the one-shot 63. This cross connection between the one-shots 63 and 64 assures that when the Q output of either is a high state, then the other cannot have its Q output go high. The output of the one-shot 64 is a wrinkle pulse shown on curve D. This wrinkle 156 is of sufficient duration so that the one-shot 63 is disabled when it received its trigger pulse from comparator 55 which is caused by the positive going part 153 of the wrinkle signal.

A hole signal includes the positive pulse 150 followed by the negative pulse 151, shown in curve B of FIG. 7. This hole signal will first cause the voltage comparator 55 to output a pulse 158 shown at curve I on FIG. 7. The output pulse from comparator 55 causes the one-shot 63 to output a pulse 159, called a hole pulse, and this pulse 159 disables the one-shot 64 from outputting a pulse for the negative going part 151 of the hole signal.

As the leading edge 14 of the web is scanned, comparators 57 and 58 both will output a pulse, because this is a negative going web edge signal 141 shown in curve B. Comparators 55 and 56 will output a pulse when the trailing edge 15 of the web is scanned in accordance with the positive going web edge signal 143. Since the outputs of comparators 56 and 57 are normally low, the output of the NOR gate 85 is normally high. An output from either comparator 56 or 57, signalling either a trailing or a leading web edge, causes the output of NOR gate 85 to go low and this will trigger the one-shot 86. On the Q output of one-shot 86 a web edge pulse 161 will be developed, as shown at curve G in FIG. 7, on output terminal 87. This may be used to control the lateral position of the web travelling through the apparatus.

The circuit 50 distinguishes between a hole and a trailing web edge, both of which have positive going pulses initially. The hole pulse is an output by the one-shot 63. This hole pulse is delayed by the one-shot 67 which has an output pulse 162 as shown in curve K.

This pulse triggers the one-shot 69 which has an output pulse 163 as shown in curve L. These one-shots 67 and 69 delay the pulse signifying a hole. If the NOR gate 71 receives a hole pulse and a web edge pulse at the same time, the output is unchanged. This would be the case at the end of the curves L and G of FIG. 7. The $\bar{Q}$ output of one-shot 69 is normally high and this disables the NOR gate 71. The web edge pulse 161, it will be noticed, goes high before the pulse 163 from one-shot 169 goes low. As long as one input to the NOR gate 71 remains high, this gate remains disabled and no output is supplied to the hole count output terminal 75, curve M. If the NOR gate 71 receives only a hole pulse 163, as shown in the middle of curve L, then this is passed through NOR gates 72, 73 and amplifier 74 to terminal 75 as a hole count output pulse 164.

The same operation takes place for a negative going web edge which will occur at the leading edge 14 of the web. For this leading edge of the web comparators 57 and 58 both have an output and the output from comparator 57 passes through NOR gate 85 to appear as a web edge pulse 161 on curve G. The wrinkle signal has a negative going pulse 152 initially, and the output pulse 155 from comparator 58 is shown on curve C. This gives the output pulse 156 from one-shot 64, as shown in curve D. The delay one-shot 68 has an output pulse 166 as shown in curve E and this causes a delayed output pulse 167 from one-shot 70, as shown in curve F. This is passed by the NOR gate 76, 77, 78 and amplifier 79 to appear on terminal 80 as a wrinkle count output pulse 168, shown in curve H.

The circuit 50 distinguishes between a wrinkle and a leading web edge, both of which have negative going initial pulses. For the negative going web edge pulse 141, curve B, comparator 58 emits a pulse 169, curve C, and one-shot 64 emits a pulse 170, curve D. The one-shot 68 emits a pulse 171, curve E, and the delay one-shot 70 emits a delayed pulse 172, curve F. This does not produce a wrinkle count output at terminal 80. The reason is that pulse 161, curve G, from the one-shot 86 goes high on the NOR gate 76 before the negative going pulse 172 is applied to this NOR gate from one-shot 70. Thus the web edge signal 161 maintains the NOR gate disabled so that there is no wrinkle count output.

The amplifier 51 converts the sinusoidal mirror drive signal into a square wave called a mirror signal. This signal is used to turn on and off the one-shots 69 and 70 and also to reset the flip flops 89 and 90. The turning off of the one-shots 69 and 70 means that the scan is effective only when scanning from the leading edge 14 to the trailing edge 15 and during the last half of the period of oscillation the system is shut off. This establishes 100 percent inspection of the web 13.

Figure 8:
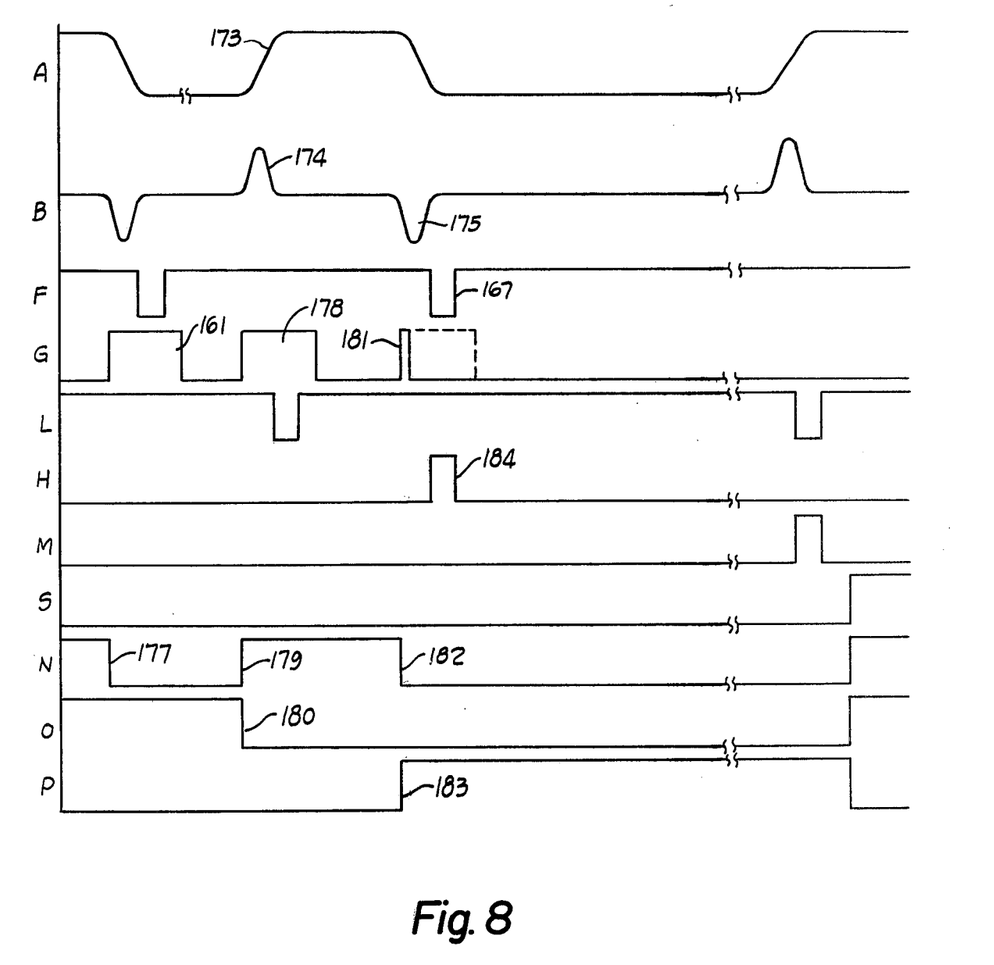
FIG. 8 is a still further graph explaining the operation under different conditions.

Occasionally a large hole will occur that produces a hole signal that is large enough to look like a web edge to the voltage comparator 56, and therefore this signal will not cause a hole output pulse. An example is shown as illustrated in FIG. 8. In this FIG. 8 wave form A is the raw signal from the detector 27. This raw signal has a large hole signal 173 present. Curve B at the terminal 45 thus has a positive going pulse 174 and a negative going pulse 175 at the beginning and end of this large hole. The other curves in FIG. 8 are curves of the pulses present at the correspondingly lettered portions of FIGS. 4 and 5. With a large hole signal present, the flip flops 89 and 90 in the edge counter circuit 88 count the number of web edges per scan. If the count is larger than two, the flip flops 89 and 90 cause the NOR gates 92 and 93 to reset the one-shot 86. This allows one extra hole pulse to be passed to the output terminal 75 to replace the one that was lost due to the circuit of FIG. 5 counting the large hole as an edge of a web. The flip flops 89 and 90 are reset after each scan.

The action of the edge counter circuit 88 is that the one-shot 86 emits a pulse 161 as the leading edge of the web is scanned. This clocks the flip flop 89 so that the $\bar{Q}$ output, shown in curve N, goes low at 177. When the large hole edge is scanned at the positive pulse 174, another web edge pulse is emitted by the one-shot 86, pulse 178. This causes the $\bar{Q}$ output of one-shot 89 to go high, at 179 of curve N, causing the $\bar{Q}$ output of flip flop 90 to go low, at 180 of curve O. When the other edge of the large hole is scanned at negative pulse 175, the one-shot 86 has a web edge pulse 181, curve G. The one-shot 89 is again triggered with $\bar{Q}$ going low at 182, curve N, which signal passes through the NOR gate 92 to make the large defect output 94 to high at 183, curve P. The output of NOR gate 93 goes low to turn off the one-shot 86 and thus to make the pulse 181 a very short pulse. Comparing curves F and G, one sees that the delayed pulse 167 from the hole counter pulse one-shot 70 will now not be masked by the pulse 181 and instead will pass a pulse 184 to the hole count output terminal 75.

Curve S shows the output of the squarer 51. At the end of half the period of oscillation, the output of squarer 51 goes low on conductor 52. Acting through NOR gate 103, this is a high to reset the one-shots 69 and 70 so there is no output during return of the scan.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the circuit and the combination and arrangement of circuit elements may be resorted to without departing from the spirit and scope of the invention as hereinafter claimed.

What is claimed is:

1. A web scanning apparatus for a web movable along a path, comprising, in combination,
   a radiation detector,
   scanning means to establish a flying spot scanning path to periodically scan transversely of the moving web from a point preceding one side of the web and across the web to a point beyond the other side of the web to thus also scan a dark background on either side of the web,
   means to irradiate at least the flying spot scanned portion of the web,
   means to transmit to said detector the image of the flying spot scanned portion of the web,
   a differentiator connected to differentiate the output of said detector, and
   an output characterization circuit connected to the output of said differentiator to characterize between increasing and decreasing signals relative to a normal output from said detector during scan of the web signalling a wrinkle and a hole, respectively, in the web.

2. A web scanning apparatus as set forth in claim 1, including an infrared passing and ultraviolet blocking filter positioned in said scanning path.

3. A web scanning apparatus as set forth in claim 1, wherein said output characterization circuit is rendered operative completely to said other side of the web for 100% transverse inspection of the web.

4. A web scanning apparatus as set forth in claim 1, including an amplifier connected to the output of said differentiator, and
   a noise discriminator connected to the output of said amplifier and supplying said output characterization circuit.

5. A web scanning apparatus as set forth in claim 1, wherein said output characterization circuit includes first and second multivibrators connected to receive the output of said differentiator to establish said first multivibrator with an output upon said differentiator emitting a positive initial pulse and to establish said second multivibrator with an output upon said differentiator emitting a negative initial pulse.

6. A web scanning apparatus as set forth in claim 1, wherein said output characterization circuit includes first and second voltage comparators,
   bias means connected to said voltage comparators to establish said first and second comparators with an output pulse upon the input changing from negative to positive and from positive to negative, respectively,
   first and second one-shot multivibrators connected to the outputs of said first and fourth comparators, respectively, to establish said first one-shot with an output upon said first comparator having a positive pulse and said second one-shot with an output upon said second comparator having a negative pulse, and
   cross connections between said first and second one-shots for the one first having an output to disable the other to distinguish between a hole in the web, with a positive initial pulse, and a wrinkle in the web, with a negative initial pulse.

7. A web scanning apparatus as set forth in claim 1, wherein said output characterization circuit includes,
   means to initiate a normal output upon the scan of the scanning path onto a leading edge of the web and to terminate the output upon the scanning path leaving the trailing edge of the web so as to automatically adjust the effective width of the scanning path in accordance with the actual width of the moving web.

8. A web scanning apparatus as set forth in claim 1, wherein said output characterization circuit includes means to discriminate between a hole in the web and a wrinkle in the web as rapidly increased or decreased reflectance of radiation, and
   said output characterization circuit including an automatic gain control circuit controlled in accordance with formation of the web or other changes of reflectance which occur at a slower rate than detection of holes and wrinkles.

9. A web scanning apparatus as set forth in claim 8, including a sampling circuit sampling the radiation received from a first predetermined portion of the width of the web in order to set the value of said automatic gain control for the entire scanning path across the web.

10. A web scanning apparatus as set forth in claim 9, including time delay means controlled by said sampling circuit to maintain substantially constant automatic gain control for the scan of the entire web width even after said predetermined width has been scanned.

11. A web scanning apparatus as set forth in claim 1, wherein said output characterization circuit includes,
    first multivibrator means to establish a wide pulse upon scanning of an edge of the web,
    second multivibrator means to establish a narrower pulse upon scanning of a defect, and
    a gate having an input from each of said multivibrator means.

12. A web scanning apparatus as set forth in claim 11, wherein said gate is disabled by a wide pulse from scanning an edge of the web to have no output pulse.

13. A web scanning apparatus as set forth in claim 11, wherein said second multivibrator means establishes a pulse delayed relative to that of said first multivibrator means.

14. A web scanning apparatus as set forth in claim 1, wherein said output characterization circuit includes an analog audio alert output upon scanning a defect in the web.

15. A web scanning apparatus as set forth in claim 1, wherein said output characterization circuit includes a marking device to mark the web at the longitudinal position therealong at which a defect is detected so as to be able to determine the defect in the rolled up web product.

16. A web scanning apparatus as set forth in claim 15, including marking the edge of the web with two different colors to identify two different types of defects.

* * * * *